United States Patent [19]

Barstad et al.

[11] Patent Number: 5,268,454
[45] Date of Patent: Dec. 7, 1993

[54] COMPOSITION FOR INDUCING HUMORAL ANERGY TO AN IMMUNOGEN COMPRISING A T CELL EPITOPE-DEFICIENT ANALOG OF THE IMMUNOGEN CONJUGATED TO A NONIMMUNOGENIC CARRIER

[75] Inventors: Paul A. Barstad, Escondido; Gilbert M. Iverson, Del Mar, both of Calif.

[73] Assignee: La Jolla Pharmaceutical Company, San Diego, Calif.

[21] Appl. No.: 652,648

[22] Filed: Feb. 8, 1991

[51] Int. Cl.$^5$ .................. C07K 17/08; C07K 17/14
[52] U.S. Cl. .................. 530/403; 530/402; 530/412; 530/868; 424/88
[58] Field of Search .................. 424/88, 86.1; 530/402, 530/403, 868, 412

[56] References Cited

U.S. PATENT DOCUMENTS

| | | | |
|---|---|---|---|
| 4,722,899 | 2/1988 | Hamooka | 435/172.2 |
| 4,950,469 | 8/1990 | Katz | 424/85.1 |
| 4,950,713 | 8/1990 | Katz | 525/54.1 |

OTHER PUBLICATIONS

W. Y. Lee, et al. Nature 267:618-619, Jun. 1987 "Abrogation of reaginie antibodies with modified allergens".
A. H. Sehon, Prog. Allergy 32:161-202 (1982) "Suppression of Iae Antibody Responses with Tolerogenic Conjugates of Allergens and Haptens".
A. H. Sehon, Adv., Exp. med. Biol. 251:341-351 (1988) "Modulation of antibody responsies by conguates of antigens with monomethoxypolyethylene glycol".
E. Wünsch, et al. Int. J. Peptides Res. 37:90-102 (1991) "Fully Synthetic immunogens".
H. M. Dintzis et al., *Proc. Natl. Acad. Sci. USA* (1976) 73(10):3671-3675.
R. Z. Dintzis et al., *J. Immunol.* (1983) 131(5):2196-2203.
R. Z. Dintzis et al., *J. Immunol.* (1985) 135(1):423-427.
R. Z. Dintzis et al., *J. Immunol.* (1989) 143(4):1239-1244.

*Primary Examiner*—Christine M. Nucker
*Assistant Examiner*—T. Cunningham
*Attorney, Agent, or Firm*—Morrison & Foerster

[57] ABSTRACT

Conjugates of stable nonimmunogenic polymers and analogs of immunogens that possess the specific B cell binding ability of the immunogen but lack T cell epitopes and which, when introduced into individuals, induce humoral anergy to the immunogen are disclosed. Accordingly, these conjugates are useful for treating antibody-mediated pathologies that are caused by foreign or self immunogens.

11 Claims, 5 Drawing Sheets

COMPOSITION FOR INDUCING HUMORAL ANERGY TO AN IMMUNOGEN COMPRISING A T CELL EPITOPE-DEFICIENT ANALOG OF THE IMMUNOGEN CONJUGATED TO A NONIMMUNOGENIC CARRIER

TECHNICAL FIELD

This invention is in the field of immunology and concerns compositions and methods for inducing humoral energy for the purpose of treating antibody-medicated pathologies. More specifically, the invention relates to conjugates of nonimmunogenic stable polymers and analogs of immunogens that lack T cell epitopes.

BACKGROUND OF THE INVENTION

In order to survive in a world of pathogenic or potentially pathogenic microorganisms, higher organisms have evolved immune systems which can specifically recognize virtually any foreign substance through its characteristic molecules. This recognition frequently results in the production of specific proteins called antibodies which bind only to the foreign substance which induced their synthesis, causing the elimination of the invading microorganism. Occasionally an animal's immune system makes antibodies which recognize some of its own molecules, generating an autoimmune state that may affect the animal's health adversely.

The induction of specific antibodies in response to an immunogen involves the interaction of multiple cell types, including thymus-derived lymphocytes (T cells), macrophages, and bone marrow-derived lymphocytes (B cells). B cellspossess surface immunoglobulin by which they are able to bind immunogens, the first step in their activation and clonal expansion The site(s), region(s) or domain(s) of the immunogen to which the immunoglobulin binds is called a "B cell epitope". In the second step of B cell activation and expansion, T cells are activated through interaction with the B cell bound-immunogen at a site, region or domain of the immunogen called a "T cell epitope". Once activated, the T cells provide positive signal(s) to the B cells to which the immunogen is bound and they proceed to differentiate and to produce and secrete antibody Positive signals from the T cell include the secretion of lymphokines, and/or direct contact between the B cells and T cells. T cell epitopes may be different or more restricted in scope than B cell epitopes. As discussed above, in order for an immunogen to elicit T dependent antibodies, it must have epitopes recognized by both B and T cells.

Past attempts to treat antibody-mediated pathologies have involved both general and specific suppression of the immune response. General suppression has typically employed broad spectrum, nonspecific immunosuppressants such as cyclophosphamide or steroids. Because these nonspecific drugs suppress many aspects of the immune system, they eliminate its required and beneficial functions as well as the malfunction causing the condition being treated. They are thus used with extreme caution, if at all, and subject the patient to risk from secondary infections or other undesirable side effects.

Because of the disadvantages of general immunosuppression, methods for specifically suppressing an immune response to an immunogen without affecting the normal functions of the immune system are highly preferred for treating antibody-mediated pathologies. The present invention concerns compositions and methods for specifically suppressing the humoral response to immunogens.

Prior attempts to induce specific immunosuppression have focused on conjugating haptens and immunogens to nonimmunogenic polymeric carriers. Benacerraf, Katz and their colleagues used conjugates of haptens and antigens and copolymers of D-lysine and D-glutamic acid (D-EK). Their initial studies involved conjugates of the synthetic hapten 2,4-dinitrophenyl (DNP) in guinea pigs and mice and showed the conjugates were capable of inducing humoral unresponsiveness. These initial studies were then extended to conjugates of other haptens and conjugates of immunogens. While the results with haptens were repeatable, and although their patents (U.S. Pat. Nos. 4,191,668 and 4,220,565) allege the approach is effective in inducing tolerance to immunogens, subsequent work has shown that conjugates of D-EK and immunogens do not provide a means for inducing humoral unresponsiveness to the immunogen. For instance, Liu et. al., *J. Immun.* (1979) 123:2456–2464, report that subsequent studies of those conjugates demonstrate that the conjugates "do not induce unresponsiveness at the level of protein specific B cells." Similarly, Butterfield et. al., *J. Allergy Clin. Immun.* (1981) 67:272–278, reported that conjugates of ragweed immunogen and D-EK actually stimulated both IgE and IgG responses to the immunogen.

This subsequent work and other data dealing with conjugates of nonimmunogenic polymers and immunogens (Saski et. al., *Scand. J. Immun.* (1982) 16:191–200; Sehon, *Prog. Allergy* (1982) 32:161–202; Wilkinson et. al., J. *Immunol.* (987) 139:326–331, and Borel et. al., *J. Immunol. Methods* (1990) 126:159–168) appear to indicate that the anergy, if any, obtained with such conjugates is due to suppression by T cell activity, not B cell unresponsiveness.

Several other references deal with conjugates of nonimmunogenic polymers and DNA. See U.S. Pat. Nos. 4,191,668; U.S. Pat. No. 4,650,625; *J. Clin. Invest.* (1988) 82:1901–1907; and commonly owned U.S. Pat. application Ser. No. 07/494,118. As a whole, these references indicate that these DNA conjugates may suppress the production of antibodies to this lupus autoimmunogen. It should be noted in this regard that DNA, like haptens, does not possess T cell epitopes.

In sum, applicants believe the prior art shows that antibody production to conjugates of nonimmunogenic stable polymers and haptens or DNA, neither of which have T cell epitopes, may provide B cell unresponsiveness. Applicants also believe that conjugates of immunogens do not provide B cell unresponsiveness but may activate T cells to directly suppress the immune response.

DISCLOSURE OF THE INVENTION

The present invention resides in the discovery that the failure of the prior conjugates of nonimmunogenic stable polymers and immunogens to induce B cell anergy (unresponsiveness) was due to the fact that the immunogens contained both B and T cell epitopes and that if the latter were eliminated, the conjugate would be effective for inducing B cell anergy.

Accordingly, one aspect of the invention is a composition for inducing specific B cell anergy to an immunogen comprising a conjugate of a nonimmunogenic biologically stable carrier polymer and an analog of the immunogen that (a) binds specifically to B cells to which the immunogen binds and (b) lacks the T cell epitope(s) of the immunogen.

Pharmaceutical compositions of the above-described conjugates and pharmaceutically acceptable carriers or vehicles are another aspect of the invention.

A further aspect of the invention is a method of inducing specific B cell anergy to an immunogen in an individual comprising administering to the individual an effective amount of the above-described conjugate.

Yet another aspect of the invention is a method of treating an individual for an antibody-mediated pathology in which undesired antibodies are produced in response to an immunogen comprising administering to the individual a therapeutically effective amount of the above-described conjugate.

MODES FOR CARRYING OUT THE INVENTION

Figure 1:
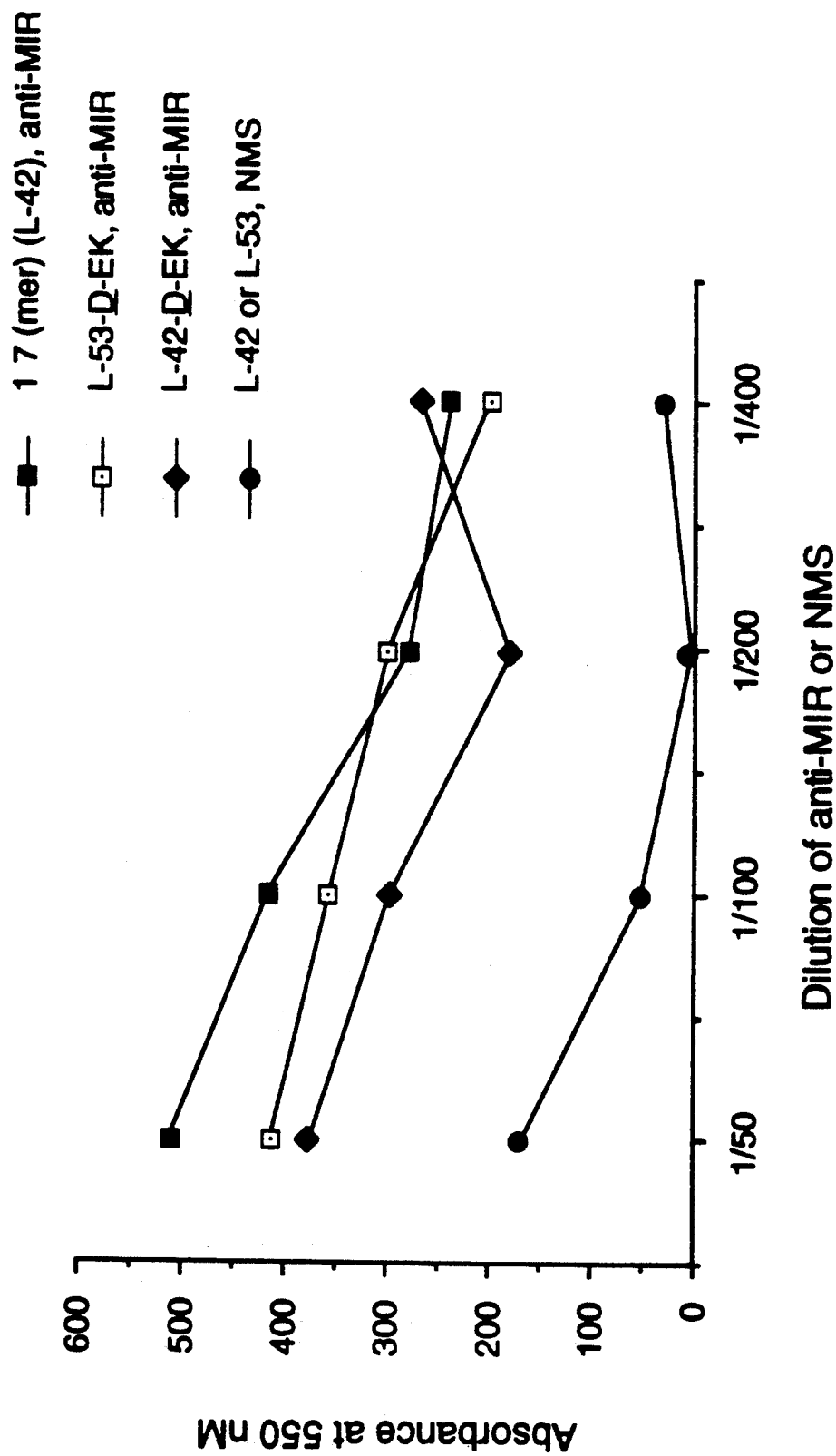
FIG. 1 graphically illustrates the detection of B cell epitopes in immunized CAF1 mice as described in Example 1. The unconjugated 17 per peptide (L-42) and L-42 and L53 conjugates were tested for B cell epitopes with anti-MIR sera. Unconjugated L-42 and L-53 were tested with normal mouse serum (NMS) as a control.

As used herein the term "B cell anergy" intends unresponsiveness of those B cells requiring T cell help to produce and secrete antibody and includes, without limitation, clonal deletion of immature and/or mature B cells and/or the inability of B cells to produce antibody. "Unresponsiveness" means a therapeutically effective reduction in the humoral response to an immunogen. Quantitatively the reduction (as measured by reduction in antibody production) is at least 50%, preferably at least 75%, and most preferably 100%.

"Antibody" means those antibodies which are T cell dependent.

As used herein the term "immunogen" means a chemical entity that elicits a humoral immune response when injected into an animal. Immunogens have both B cell epitopes and T cell epitopes.

As used herein "individual" denotes a member of the mammalian species and includes humans, primates, mice and domestic animals such as cattle and sheep, sports animals such as horses, and pets such as dogs and cats.

The term "analog" of an immunogen intends a molecule that (a) binds specifically to an antibody to which the immunogen binds specifically and (b) lacks T cell epitopes. Although the analog will normally be a fragment or derivative of the immunogen and thus be of the same chemical class as the immunogen (e.g., the immunogen is a polypeptide and the analog is a polypeptide), chemical similarity is not essential. Accordingly, the analog may be of a different chemical class than the immunogen (e.g., the immunogen is a carbohydrate and the analog is a polypeptide) as long as it has the functional characteristics (a) and (b) above. The analog may be a protein, carbohydrate, lipid, lipoprotein, glycoprotein, lipopolysaccharide or other biochemical entity. Further, the chemical structure of neither the immunogen nor the analog need be defined for the purposes of this invention.

"Nonimmunogenic" is used to describe the carrier polymer means that the carrier polymer elicits substantially no immune response when it is administered by itself to an individual.

Immunogens that are involved in antibody mediated pathologies may be external (foreign to the individual) immunogens such as biological drugs, allergens, idiopathic contrast media, and the like or self-immunogens (autoimmunogens) such as those associated with thyroiditis (thyroglobulin), stroke (cardiolipin), male infertility ($\alpha$-sperm), myasthenia gravis (acetylcholine receptor), rheumatic fever (carbohydrate complex), and Rh hemolytic disease (D immunogen).

Analogs to such immunogens may be identified by screening candidate molecules to determine whether they (a) bind specifically to serum antibodies to the immunogen and (b) lack T cell epitopes. Specific binding to serum antibodies may be determined using conventional immunoassays and the presence or absence of T cell epitopes may be determined by conventional T cell activation assays. In this regard an analog which "binds specifically" to serum antibodies to the immunogen exhibits a reasonable affinity thereto. The presence or absence of T cell epitopes may be determined using the tritiated thymidine incorporation assay described in the examples. Analogs that fail to induce statistically significant incorporation of thymidine above background are deemed to lack T cell epitopes. It will be appreciated that the quantitative amount of thymidine incorporation may vary with the immunogen. Typically a stimulation index below about 2-3, more usually about 1-2, is indicative of a lack of T cell epitopes.

A normal first step in identifying useful analogs is to prepare a panel or library of candidates to screen. For instance, in the case of protein or peptide analogs, libraries may be made by synthetic or recombinant techniques such as those described by Geysen et. al. in *Synthetic Peptides as Antigens;* Ciba Symposium (1986) 119:131-149; Devlin et. al., Science (1990) 249:404-406; Scott et. al., Science (1990) 249:386-390; and Cwirla et. al., PNAS USA (1990) 87:6378-6382. In One synthetic technique, peptides of about 5 to 30 amino acids are synthesized in such a manner that each peptide overlaps the next and all linear epitopes are represented. This is accomplished by overlapping both the carboxyl and amino termini by one less residue than that expected for a B cell epitope. For example, if the assumed minimum requirement for a B cell epitope is six amino acids, then each peptide must overlap the neighboring peptides by five amino acids. In this embodiment, each peptide is then screened against antisera produced against the native immunogen, either by immunization of animals or from patients, to identify the presence of B cell epitopes. Those molecules with antibody binding activity are then screened for the presence of T cell epitopes as described in the examples. The molecules lacking T cell epitopes are useful as analogs in the invention.

If the T cell epitope(s) of an immunogen are known or can be identified, T cell random screening of candidate analogs is not necessary. In such instances, the T cell epitope(s) may be altered (e.g., by chemical derivatization, or elimination of one or more components of the epitope) to render them inoperative or be eliminated completely, such as, for instance, in the case of peptides, by synthetic or recombinant procedures.

The analogs are coupled to a nonimmunogenic polymeric carrier to prepare the conjugates of the invention. Preferred polymeric carriers are biologically stable, i.e., they exhibit an in vivo excretion half-life of days to months, and are preferably composed of a synthetic single chain of defined composition. They will normally have a molecular weight in the range of about 5,000 to about 200,000, preferably 5,000 to 30,000. Examples of such polymers are polyethylene glycol, poly-D-lysine, polyvinyl alcohol, polyvinyl pyrrolidone, immunoglobulins, and "D-EK", a copolymer of D-glutamic acid and D-lysine. Particularly preferred carrier polymers are D-EKs having a molecular weight of about 5,000 to about 30,000, and an E:K (D-glutamic acid:D-lysine) mole ratio of approximately 60:40, as described in U.S. Patent Application Serial No. 07/494,118, referenced above.

Conjugation of the analog to the carrier polymer may be effected in any number of ways, typically involving one or more crosslinking agents and functional groups on the analog and carrier.

Polypeptide analogs will contain amino acid sidechain groups such as amino, carbonyl, or sulfhydryl groups that will serve as sites for coupling the analog to the carrier. Residues that have such functional groups may be added to the analog if the analog does not already contain same. Such residues may be incorporated by solid phase synthesis techniques or recombinant techniques, both of which are well known in the peptide synthesis arts. In the case of carbohydrate or lipid analogs, functional amino and sulfhydryl groups may be incorporated therein by conventional chemistry. For instance, primary amino groups may be incorporated by reaction with ethylendiamine in the presence of sodium cyanoborohydride and sulfhydryls may be introduced by reaction of cysteamine dihydrochloride followed by reduction with a standard disulfide reducing agent. In a similar fashion the carrier may also be derivatized to contain functional groups if it does not already possess appropriate functional groups. With specific reference to conjugating peptide analogs and D-EK or other proteinaceous carriers, coupling is preferably carried out using a heterobifunctional crosslinker, such as sulfosuccinimidyl(4-iodoacetyl) aminobenzoate, which links the $\epsilon$ amino group on the D-lysine residues of D-EK to a sulfhydryl side chain from an amino terminal cysteine residue on the peptide to be coupled. This method is preferably carried out such that an average of 3 to 5 analog molecules are coupled to each D-EK molecule and the average molecular weight of the D-EK prior to coupling is 5,000 to 30,000 daltons.

The conjugates will normally be formulated for administration by injection (e.g., intraperitoneally, intramuscularly, etc.). Accordingly, they will typically be combined with pharmaceutically acceptable carriers such as saline, Ringer's solution, dextrose solution, and the like. The conjugate will normally constitute about 0.01% to 10% by weight of the formulation. The conjugate is administered to an individual in a "therapeutically effective amount", i.e., an amount sufficient to produce B cell anergy to the involved immunogen and effect prophylaxis, improvement or elimination of the antibody-mediated condition being addressed. The particular dosage regimen, i.e., dose, timing and repetition, will depend on the particular individual and that individual's medical history. Normally, a dose of about 10 $\mu$g to 1 mg conjugate/kg body weight will be given, daily for three consecutive days. Other appropriate dosing schedules would be 3 doses per week, or one dose per week. Repetitive administrations, normally timed according to B cell turnover rates, may be required to achieve and/or maintain a state of humoral anergy. Such repetitive administrations will typically involve treatments of up to 1 mg/kg of body weight every 30 to 60 days, or sooner, if an increase in antibody titer is detected. Alternatively, sustained continuous release formulations of the conjugates may be indicated for some pathologies. Various formulations and devices for achieving sustained release are known in the art.

Anti-T helper cell treatments may be administered together with the conjugates. Such treatments usually employ agents that suppress T cells such as steroids or cyclosporin.

The following examples are intended to further illustrate the invention and its uniqueness. These examples are not intended to limit the scope of the invention in any manner.

EXAMPLE 1

B Cell Anergy to the Acetylcholine Receptor

Preparation of Peptides and D-EK/Peptide Conjugates:

The $\alpha$-subunit of the acetylcholine receptor of *Torpedo californicus* is described by Stroud, R. M., and Finer-Moore, J., *Ann. Rev. Cell Biol.* (1985) 1:317:351, and Sumikawa, K., et. al., *Nucl. Acids Res.* (1982) 10:5809-22. The peptide defined by residues 47-127 of that $\alpha$-subunit is called the major immunogenic region (MIR).

Two peptides, L-42 and L-53, corresponding to residues 61-77 and 112-127 of that $\alpha$-subunit, were synthesized using conventional solid-phase methods and purified to homogeneity by HPLC. An amino terminal cysteine was added to each sequence for the purpose of attachment of the peptide to D-EK via a thio ether linkage.

Each peptide (40 mg) was dissolved in 0.1M sodium borate buffer, pH 9.0. The solution was reacted with citraconic anhydride (400 $\mu$L) at room temperature; the pH was maintained above 7.0 by addition of IM NaOH. The solution was then made 20 mM in dithiothreitol and was warmed at 37° C. for 20 minutes to reduce the peptide. The mixture was quickly desalted over G-10 Sephadex columns which were equilibrated with 0.1M sodium borate, pH 7.0.

D-EK (200 mg, weight average mw$\simeq$10,000-30,000) was dissolved in 2.0 mL of 0.1M sodium borate. Sulfosuccinimidyl (4-iodoacetyl) aminobenzene (SSIAB, 10 mg, Pierce Chemical) was added to the mixture and the mixture was reacted for 90 minutes at room temperature in the dark. The mixture was then desalted over a 10 mL G-25 column, equilibrated with 0.1M sodium borate, pH 7.0.

The desalted SSIAB-D-EK was mixed with the reduced and desalted peptide and reacted overnight. The resulting conjugate was placed in dialysis tubing with a 14 Kd cutoff and was dialyzed against 5% acetic acid to remove citraconyl groups. The dialysis buffer was changed to phosphate-buffered saline and the dialysis continued.

Detection of B cell epitopes:

CAF1 mice were immunized (day 0) intraperitoneally (i.p.) with 50 $\mu$g of recombinant torpedo MIR absorbed onto alum plus B. pertussis vaccine (Iverson, G. M., (1986) Handbook of Experimental *Immunology*, Vol. 2, p. 67, D. M. Weir ed., Blackwell Scientific Publications, Palo Alto, CA). The mice received a booster injection of the same protein in saline, IP, on day 21 and were bled from the tail vein on day 28. Sera from these mice (anti-MIR sera) were used to screen peptides L-42 and L-53 for the presence of B cell epitopes, as follows. The sera were added to microtiter wells coated with 10 μg/ml of the indicated peptide conjugates. The plates were incubated at 37° C. for one hour, washed 3 times, 100 μl of alkaline phosphatase-conjugated goat antimouse antibody was added, incubated at 37° C. for one hour, washed 3 times, and 100 μl of developer (substrate) was added to each well. The plates were incubated at room temperature for 30 minutes and the amount of color in each well was determined in a Titertek ® Multiskan. Results are illustrated graphically in FIG. 1. The notation "17 mer" corresponds to the unconjugated L-42 peptide. The L-53 peptide is a 16 mer. The curve labelled "L-42 or L-53 NMS contains the values obtained using normal mouse serum (NMS) instead of the anti-MIR sera on plates coated with either L-42 or L-53. As shown in FIG. 1, both peptides reacted specifically with antibodies from the immunized mice indicating the presence of B cell epitopes on both peptides.

Figure 2:
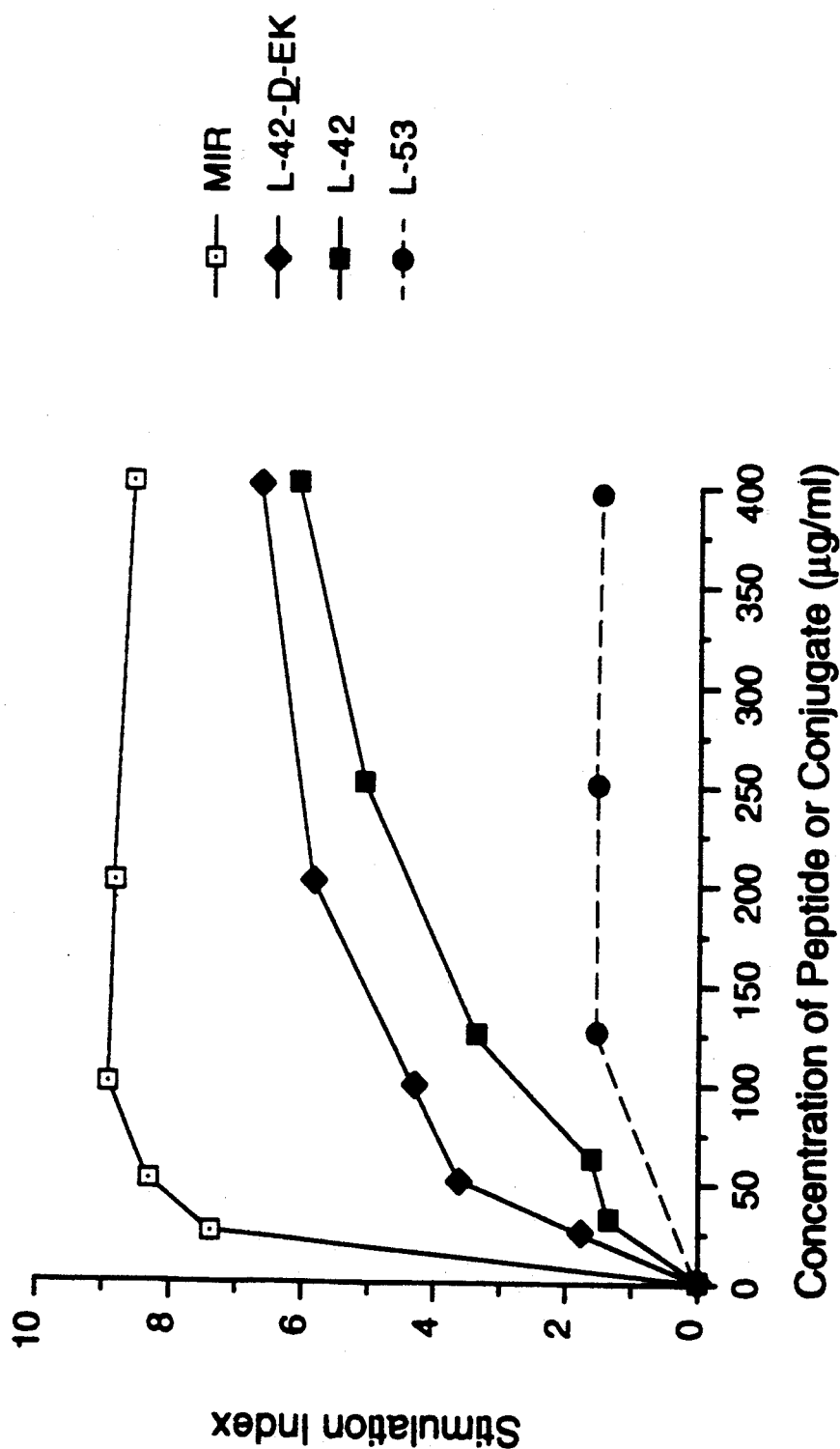
FIG. 2, similarly, illustrates the detection of T cell epitopes as described in Example 1.

Detection of T cell epitopes:

T cell activation was assayed by the general procedure of Bradley, M. L., (1980) in Mishell and Shigii, eds., *Selected Methods in Cellular Immunology* (W. H. Freeman and Co., San Francisco, CA), p. 164. CAF1 mice were immunized on the footpad with 50 μg MIR in Complete Freund's Adjuvant (CFA) on day 0. On day 7 the popliteal lymph nodes were removed and placed in culture in microtiter plates using $5 \times 10^5$ cells per well. L-42, L-53 D-EK conjugates thereof were added to the cultures, and on day 4, 1 μCi of tritiated thymidine was added to each well to measure proliferation of T cells. The cultures were harvested on a day 5 with a Skatron ® cell harvester. The amount of incorporated $^3$H-thymidine was determined in a Beckman 6800 ® liquid scintillation counter. The stimulation index was calculated by dividing the CPM incorporated with peptide by the CPM incorporated from cultures without any peptide. A stimulation index >2–3 was indicative of the presence of a T cell epitope on the peptide added to the well. As shown in FIG. 2, L-42 but not L-53 possessed T cell epitopes in this assay.

Figure 3A:
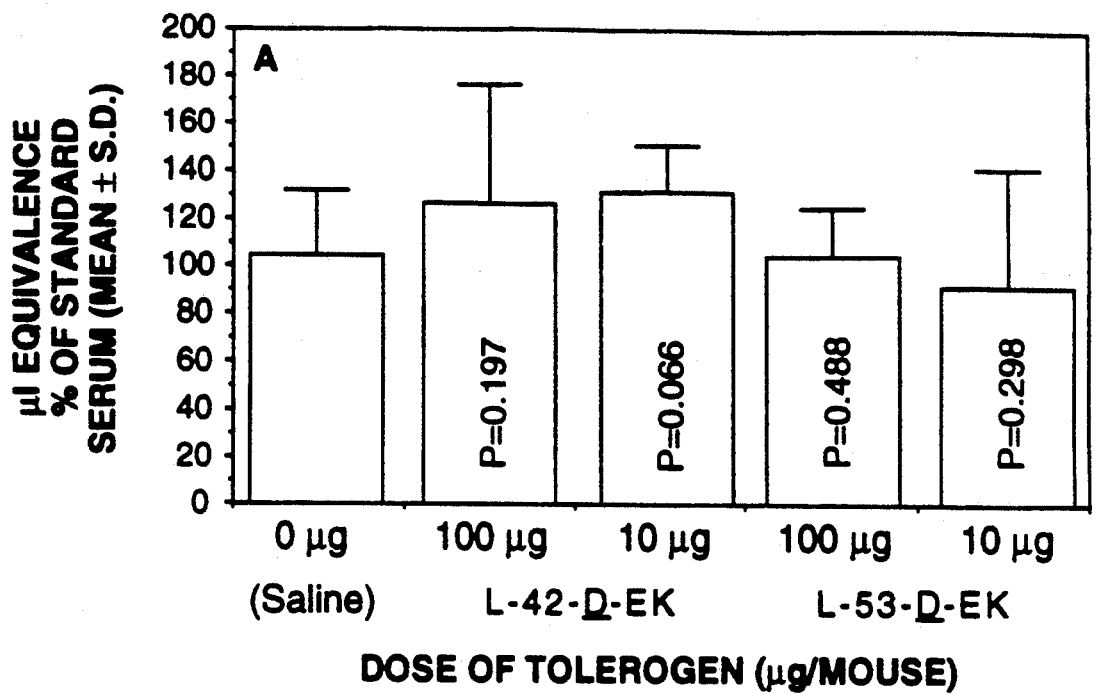
FIG. 3 illustrates the suppression of antibodies to peptide "L-53" as described in Example 1.
Figure 3B:
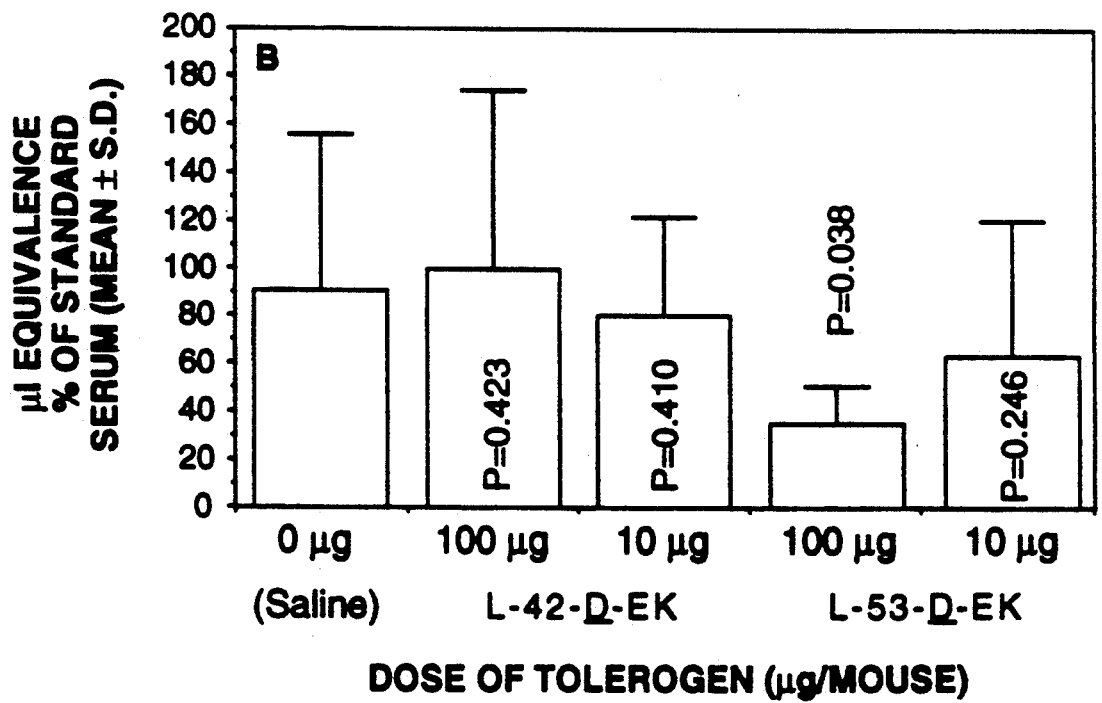
Figure 4:
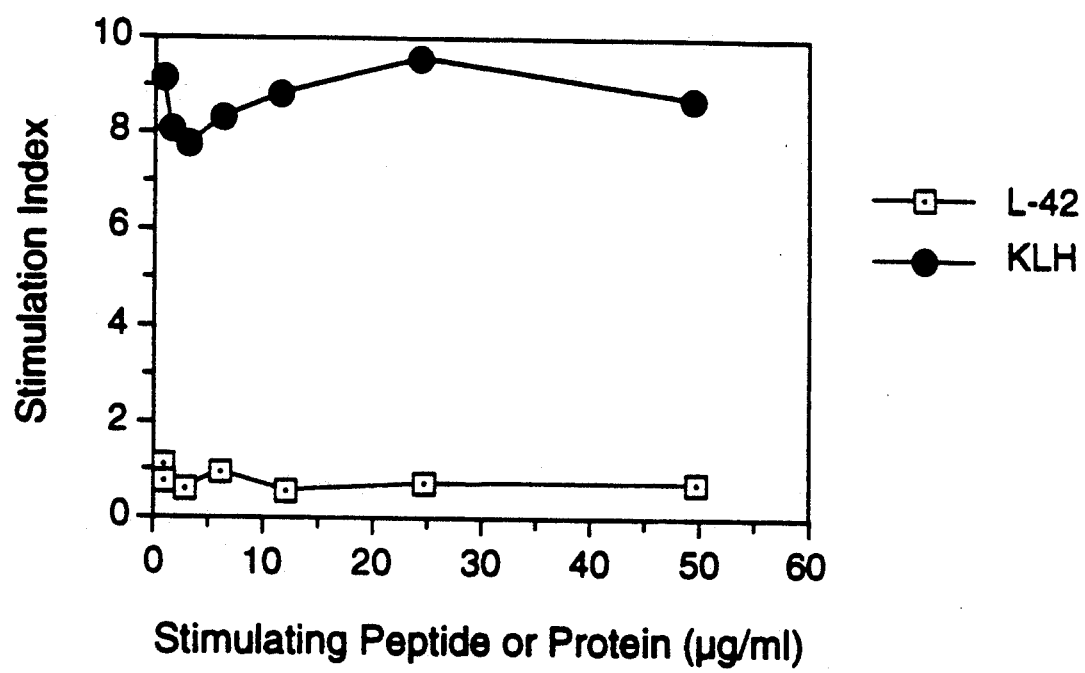
FIGS. 4 and 5 are graphs of the results described in Example 4.

Induction of B Cell Anergy to L-53 by L-53/D-EK Conjugate:

CAF1 mice were immunized with 50 μg of MIR, i.p., absorbed onto alum plus B. pertussis vaccine on day 0. On days 21, 22 and 23 the mice (6 mice per group) received 10 or 100 μg of either L-42/D-EK conjugate or L-53-D-EK conjugate. One group received only saline. On day 28 all mice received a booster injection of MIR in saline and on day 35 all mice were bled and assayed for the presence of antibodies to L-42 and L-53 in their sera, using an ELISA assay as described above with respect to FIG. 1. The results for antibodies to L-42 are shown in FIG. 3A and for antibodies to L-53 are shown in FIG. 3B. The L-53 conjugate suppressed antibody formation to L-53 but not to L-42. The L-42 conjugate did not suppress the antibody response to either L-42 or L-53 but rather may have increased antibody production to L-42. The antibody titers are expressed as a percent of a standard sera. The p values were determined by a Student t test comparing each dose to the saline control.

EXAMPLE 2

Failure of Ovalbumin-D-EK Conjugate to Induce B Cell Anergy to Ovalbumin

This example is further evidence that conjugates of immunogens and D-EK do not induce B cell anergy.

Synthesis of Ovalbumin-D-EK Conjugate:

Chicken egg ovalbumin (50 mg) was dissolved in 5 mL of 0.1M sodium borate buffer, pH 9.0, containing 10 mM EDTA. After the addition of 3.0 mg of 2-iminothiolane (Traut's reagent), the mixture was reacted for 2.5 hours at room temperature. D-EK (54 mg), dissolved in 0.5M sodium borate, pH 9.0, at a concentration of 100 mg/mL, was reacted with SSIAB (18 mg; Pierce Chemical) for 2.5 hours in the dark, at room temperature. The two reaction mixtures described above were desalted separately on G-25 columns (Pharmacia; 10 mL column volume, equilibrated with 0.1M sodium borate, pH 9.0) and the excluded fractions were combined and reacted for 16 hours at 4° C., in the dark. The reaction product was fractionated by gel filtration over Sephacryl S-200 (490 mL, Pharmacia) columns, equilibrated with 0.2M ammonium bicarbonate. Fractions containing conjugate, as assessed by polyacrylamide gel electrophoresis, in the presence of sodium dodecyl sulfate (SDS-PAGE), were pooled and dried under vacuum. The dried material was reacted with 0.8 mL of citraconic anhydride, maintaining the pH between 7 and 9 by the addition of IM NaOH, in order to efficiently separate conjugated ovalbumin from unreacted protein. The citraconylated conjugate was rechromatographed over S-200, and fractions containing high molecular weight material (>80,000 daltons), as assessed SDS-PAGE, were used for biological studies.

Chicken ovalbumin, when conjugated to D-EK, does not induce B cell anergy in mice immunized to chicken ovalbumin:

Female CAF1 mice were primed with chicken ovalbumin (ova; 100 μg/mouse, i.p.) precipitated on alum, with B. pertussis vaccine added as an adjuvant. Sixteen weeks later, the mice were divided into two groups of six mice each. One group (control) was treated with saline, and the second group was injected with a conjugate of ova and D-EK (ova-D-EK; 200 μg/mouse/day, i.p.). The mice were dosed on three successive days. One week after the first dose, the mice in both groups were boosted, i.p., with ova in saline (100 μg/mouse). One week later, the mice were bled from a tail vein. The plasma was harvested and assayed for the amount of antiova antibodies by an ELISA assay. As shown in Table 1, the ova-D-EK conjugate did not suppress the anti-ova response.

TABLE 1

| Group | Treatment | μL Equivalents[1] of Anti-Ova ± S.D. (Percent of Anti-Ova Standard[1] Serum ± S.D.) |
|---|---|---|
| 1 | saline | 70.7 ± 36 |
| 2 | ova-D-EK | 160.2 ± 167 |

[1]The amount of anti-ova antibody was determined in an ELISA, measured against a standard pool of sera obtained from CAF1 mice immunized and boosted with ova. The values shown are the mean and standard deviation for the six mice in each group.

EXAMPLE 3

Failure of MIR-D-EK Conjugate to Induce B Cell Anergy to MIR

This example is still further evidence that conjugates of immunogens and D-EK do not induce B cell anergy.

Synthesis of MIR-D-EK Conjugate:

MIR was modified on its carboxyl-terminus to include a sequence of 8-amino acids (Arg-Ser-Lys-Ser-Lys-Ser-Lys-Cys (SEQ. ID NO.: 1)). The amino-terminus was extended by one amino acid, proline. Purified modified MIR (250 mg) was reduced with 100 mM dithiothreitol and was desalted over Sephadex G-25 (Pharmacia), equilibrated with 0.1 M sodium borate buffer, pH 9.0, containing 10 mM EDTA. D-EK (400 mg) was reacted with SSIAB (29 mg) as in the previous examples. The product was desalted over G-25. The excluded volumes from the modified MIR and D-EK G-25 column runs were Excess SSIAB groups were quenched with 2-mercaptoethanol, d the reaction mixture was concentrated to 20 mL over a PM-10 membrane (Amicon Corporation). The mixture was treated with 1.0 mL of citraconic anhydride and chromatographed over S-300 (Pharmacia; 1.8 L), equilibrated with 5% ammonium hydroxide. Fractions containing two or more modified MIR groups per D-EK, as assessed by SDS-PAGE, were pooled and used for biological studies.

MIR-D-EK conjugate contains T cell epitopes in rats immunized with MIR from the same species:

T cell activation was assayed by the general procedure of Bradley, suora. Female Lewis rats were immunized in the footpad with MIR (50 μg) in complete Freund's adjuvant (CFA) on day 0. On day 7, the popliteal lymph nodes were removed and placed in culture in microtiter plates using $5.10^5$ cells per well. MIR-D-EK was added, and, after four days of culture, the wells were pulsed with tritiated thymidine (1-μCi) to measure proliferation of T cells. The cultures were collected after 5 days of culture with a Skatron ™ cell harvester. The amount of incorporated $^3$H-thymidine was determined by scintillation spectrometry. The stimulation index was calculated by dividing the counts incorporated in the absence of the conjugate. A stimulation index of greater than 2-3 was considered indicative of the presence of a T cell epitope on the added conjugate. The stimulation index was 4 or greater at all concentrations of MIR-D-EK tested (10 μg/mL to 400 mg/mL). This proves that T cells from MIR-immunized rats recognize T cell epitopes on the MIR-D-EK conjugate in this assay.

MIR-D-EK does not induce B cell anergy in rats immunized with MIR:

Female Lewis rats were primed with MIR (100 μg/rat) in CFA. Six months later, the rats were divided into three groups of three rats each. One group was treated with saline (control) and the other two groups were treated with MIR-D-EK (100 μg/rat, i.p.) on three successive days. After one week, the rats in the control group and one group that had been treated with MIR-D-EK ere boosted with recombinant MIR (1000 μg/rat, i.p.) in saline. One week later, all three groups of rats were bled from the tail vein. The plasma was harvested and assayed for the amount of anti-MIR antibodies by an ELISA assay. Table 2 below reports the data from those assays.

TABLE 2

| Group | Treatment | MIR Boost | μg/ml anti-MIR[2] (mean ± S.D.) | P vs. Group 1 |
|---|---|---|---|---|
| 1 | Saline | Yes | 130.5 ± 74.7 | |
| 2 | MIR-D-EK | Yes | 85.5 ± 31.1 | 0.195 |
| 3 | MIR-D-EK | No | 230.6 ± 31 | 0.049 |

[2] The concentration of anti-MIR antibodies was determined in an ELISA measured against a standard pool of rat anti-MIR sera. The values shown are the mean and standard deviation of the three rats in each group. P values were determined by a student t test. Group 2 is not significantly different from Group 1. Group 3 (the non-boosted group) is significantly higher than Group 1.

As shown in Table 2, the data on Group 1 animals (saline control) indicate that MIR itself is an immunogen. The data for the Group 2 and 3 animals indicate that the MIR-D-EK conjugate did not affect the anti-MIR response. In fact, MIR-D-EK boosted the anti-MIR response in Group 3.

EXAMPLE 4

Tests with Conjugate of L-42 and KLH

These tests, taken together with the results of Example 1 show that the moiety conjugated to D-EK will cause anergy in B cells recognizing that moiety if the moiety either does not contain a T cell epitope or is not recognized by T cells.

Synthesis of 17-mer (L-42) peptide-KLH conjugate:

Reduced L-42 (see Example 1) was conjugated to keyhole limpet hemocyanin (KLH) using thioether chemistry similar to that described above with respect to D-EK.

L-42 lacks a T cell epitope(s) in mice immunized with L-42-KLH:

Activation of T cells by peptides was measured by the general procedure of Bradley, supra. Female $CAF_1$ mice were immunized in the footpad with L-42 peptide conjugated KLH (L-42-KLH; 50 μg) in CFA on day 0. On day 7, the popliteal lymph nodes were removed and placed in culture in microtiter plates, at a cell density of $5.10^5$ cells/well. Peptides were added, and, after four days of culture, the wells were pulsed with 1 μCi of tritiated thymidine to measure proliferation of T cells. The cultures were collected after 5 days of culture with a cell harvester. The amount of incorporated $^3$H-thymidine was determined by scintillation spectrometry. The stimulation index was calculated by dividing the counts incorporated in the absence of peptide. An index of greater than 2–3 is indicative of the presence of a T cell epitope on the added peptide.

The data in FIG. 4 demonstrate that the L-42 did not stimulate the growth of T cells taken from L-42-KLH-immunized mice, and therefore did not contain an epitope(s) recognized by T cells induced by immunization with L-42-KLH.

L-42-D-EK conjugate induces a B cell anergy in mice immunized to L-42-KLH:

$CAF_1$ mice were primed with 100 μg/mouse of L-42-KLH on alum plus *B. pertussis* vaccine as an adjuvant. Three weeks later, the mice were divided into groups of six mice each. One group was treated by i.p. injections on three successive days with saline (control); the other groups were similarly treated with L-42-KLH (50 μg/mouse, i.p.), and, after a wait of one week, they were bled from the tail vein. The plasma was harvested and assayed for the amount of anti-L-42 antibodies by an ELISA assays. Data are expressed as a percent of a standard serum. An asterisk indicates that a data point was significantly different from the control as determined by a Student t test.

Figure 5:
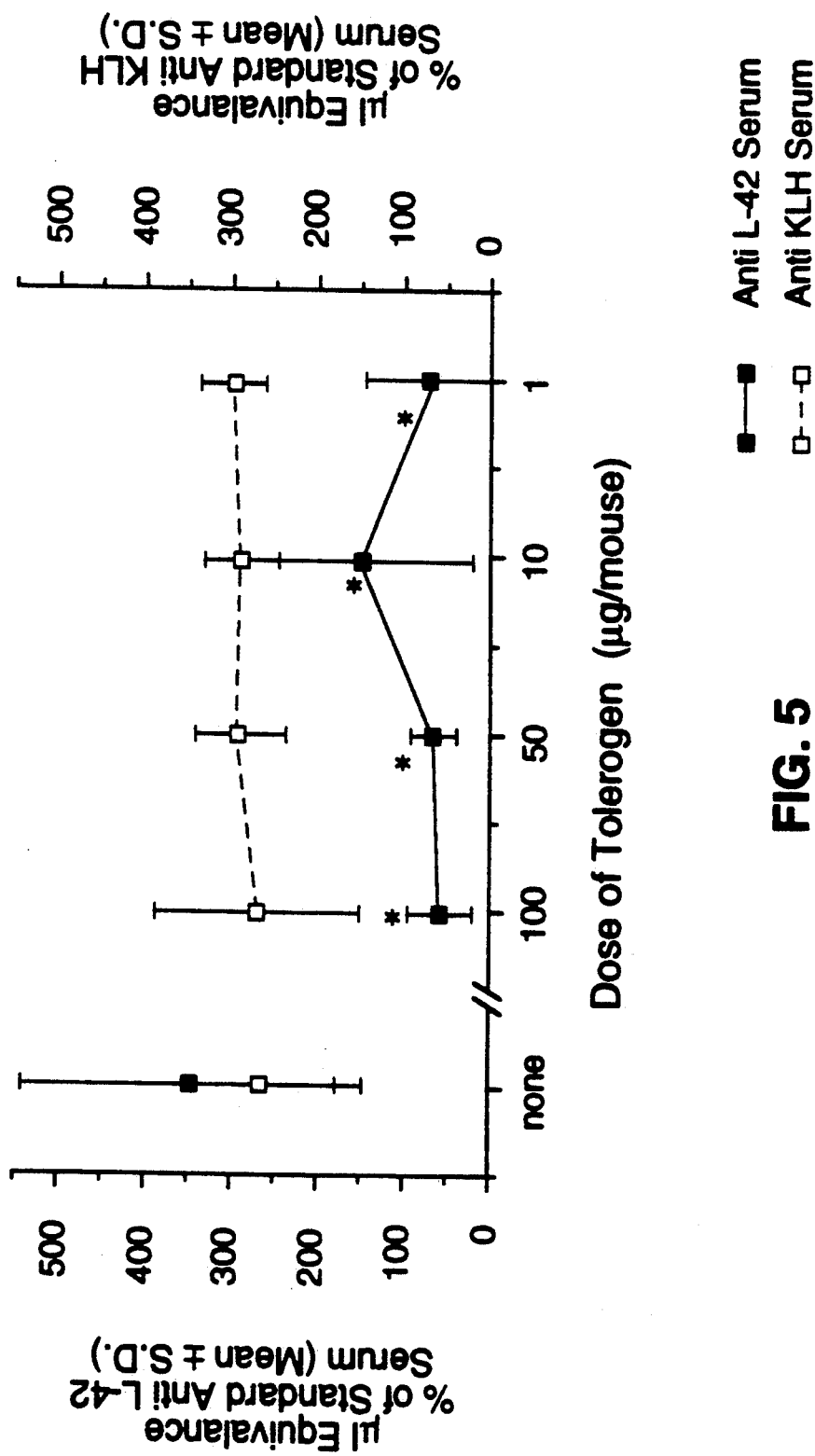

The data in FIG. 5 demonstrate that the L-42 response, but not the anti-KLH response, was suppressed in this assay by the L-42-D-EK conjugate. Thus, the studies summarized in Example 1 and these data demonstrate the L-42-D-EK induces B cell anergy when the mice are immunized in a manner that does not induce the proliferation of T cell clones that recognize the L-42 peptide On the other hand, L-42-D-EK did not induce B cell anergy in animals that were immunized with an immunogen (MIR) which induced T cells that recognized the L-42 peptide.

Modifications of the above-described modes for carrying out the invention that are obvious to those of ordinary skill in the fields of immunology, chemistry, medicine and related arts are untended to be within the scope of the following claims.

We claim:

1. A method for making a conjugate useful for inducing specific B cell anergy to an immunogen implicated in an antibody-medicated pathology, the conjugate comprising a nonimmunogenic biologically stable polymer and an analog of the immunogen wherein (i) the analog binds specifically to B cells to which the immunogen binds specifically and (ii) the conjugate lacks a T cell epitope, comprising the steps of:
   (a) convalently bonding the analog of the immunogen lacking T cell epitopes to a nonimmunogenic polymer to form a conjugate; and
   (b) separating the conjugate from the reaction mixture.

2. The method of claim 1 wherein the immunogen is an external immunogen.

3. The method of claim 2 wherein the external immunogen is a biological drug, an allergen, or an idiopathic contrast medium.

4. The method of claim 1 wherein the immunogen is a self-immunogen.

5. The method of claim 4 wherein the self-immunogen is that associated with thyroiditis, diabetes, stroke, male infertility, myasthenia gravis, rheumatic fever, or Rh hemolytic disease.

6. The method of claim 1 wherein the immunogen and analog are of the same chemical class.

7. The method of claim 6 wherein the immunogen and analog are polypeptides.

8. The method of claim 1 wherein the immunogen and analog are of different chemical classes.

9. The method of claim 1 wherein the polymer is a copolymer of d-lysine and D-glutamic acid.

10. The method of claim 1 wherein the polymer is a polyethylene glycol.

11. A method for making a composition useful for inducing specific B cell anergy to an immunogen implicated in an anti-body medicated pathology, the composition comprising a pharmaceutically acceptable vehicle and a conjugate of a nonimmunogenic biologically stable polymer and an analog of the immunogen wherein (i) the analog binds specifically to B cells to which the immunogen binds specifically and (ii) the conjugate lacks a T cell epitope, comprising the steps of:
   (a) convalently bonding the analog of the immunogen lacking T cell epitopes to an nonimmunogenic polymer to form a conjugate;
   (b) separating the conjugate from the reaction mixture; and
   (c) combining the conjugate with a pharmaceutically acceptable vehicle.

* * * * *

UNITED STATES PATENT AND TRADEMARK OFFICE
CERTIFICATE OF CORRECTION

PATENT NO. : 5,268,454

DATED : 12/07/93

INVENTOR(S) : Barstad et al.

It is certified that error appears in the above-identified patent and that said Letters Patent is hereby corrected as shown below:

Column 1, line 11, delete "antibody-medicated" and insert --antibody-mediated--;

Column 11, line 23, Claim 1, delete "antibody-medicated" and insert --antibody-mediated--;

Column 12, line 22, Claim 11, delete "anti-body medicated" and insert --antibody-mediated--

Signed and Sealed this

Twenty-fifth Day of February, 1997

Attest:

BRUCE LEHMAN

Attesting Officer

Commissioner of Patents and Trademarks